United States Patent [19]

Kaldany

[11] Patent Number: 5,082,005
[45] Date of Patent: Jan. 21, 1992

[54] SURGICAL ACCESS DEVICE

[75] Inventor: Antoine Kaldany, Chestnut Hill, Mass.

[73] Assignee: New England Deaconess Hospital, Boston, Mass.

[21] Appl. No.: 629,148

[22] Filed: Dec. 18, 1990

[51] Int. Cl.$^5$ ............................................. A61B 19/08
[52] U.S. Cl. ................................... 128/850; 604/175
[58] Field of Search ............... 128/849, 850, 853, 854; 604/93, 175

[56] References Cited

U.S. PATENT DOCUMENTS

| | | | |
|---|---|---|---|
| 3,402,710 | 9/1968 | Paleschuck . | |
| 3,752,162 | 8/1973 | Newash . | |
| 3,881,474 | 5/1975 | Krzewinski | 128/882 |
| 4,024,862 | 5/1977 | Collins | 128/854 |
| 4,059,104 | 11/1977 | DePriest et al. | 128/853 |
| 4,196,723 | 4/1980 | Moose, Jr. | 128/854 |
| 4,336,797 | 6/1982 | Latucca et al. | 128/854 |
| 4,543,088 | 9/1985 | Bootman et al. . | |
| 4,607,631 | 8/1986 | Hanssen | 128/853 |
| 4,673,394 | 6/1987 | Fenton, Jr. et al. | 604/175 |
| 4,778,452 | 10/1988 | Moden et al. . | |
| 4,802,885 | 2/1989 | Weeks et al. . | |
| 4,897,081 | 1/1990 | Poirier et al. . | |
| 4,966,168 | 10/1990 | Glassman | 128/854 |

FOREIGN PATENT DOCUMENTS 378624 6/1964 Switzerland .

OTHER PUBLICATIONS

Guide to Purchasing, 1956, p. 829, V. Mueller & Co., Chicago.

Primary Examiner—Paul J. Hirsch
Attorney, Agent, or Firm—Hamilton, Brook, Smith & Reynolds

[57] ABSTRACT

A surgical access device for subcutaneous implantation in a patient adjacent a bodily cavity. The device comprises a resilient biocompatible plate, a slit through the plate and a skirt which extends internally from the edge of the slit. The device has attachment points for securing the device subcutaneously to muscle or other tissue. The slit through the plate opens in response to an appropriate force to provide access to the bodily cavity through the skirt.

19 Claims, 2 Drawing Sheets

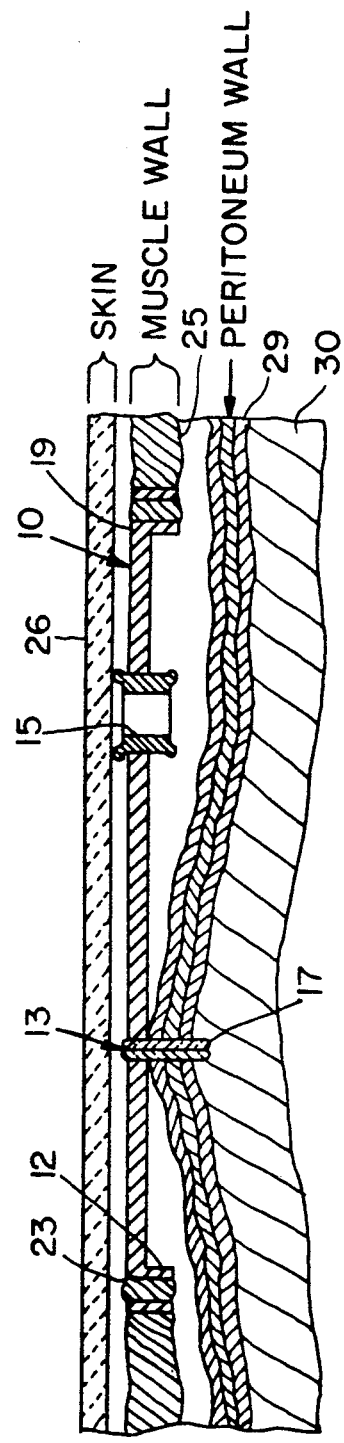
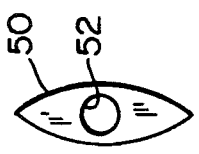
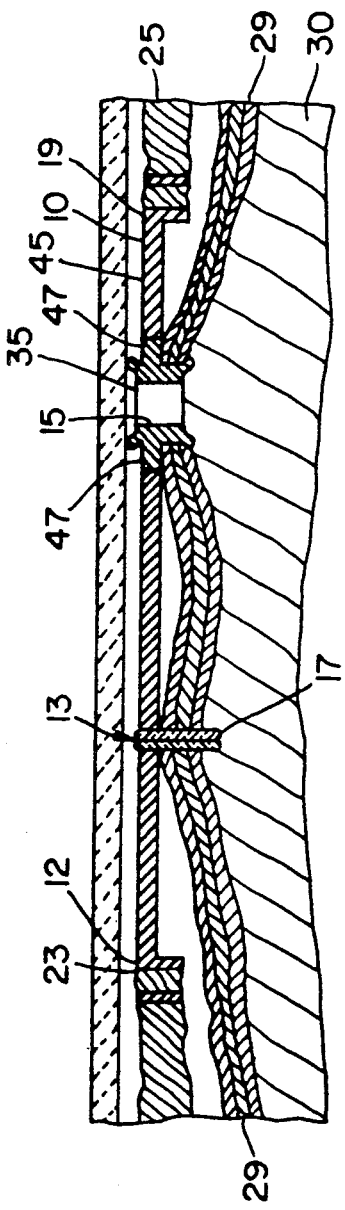

SURGICAL ACCESS DEVICE

BACKGROUND OF THE INVENTION

This invention relates to devices for providing access to a bodily cavity through the skin. Heretofore the art has generally utilized percutaneous devices for access. Percutaneous access devices are useful when frequent or long-term access to the body is required, as in kidney dialysis, drug delivery, intravenous feeding, ostomies, and transmission of energy to intra-corporeal blood pumps. Practical devices for long-term skin penetration in humans, however, have not been generally successful because skin adjacent to the implanted devices will not heal to form a tight barrier to infection. Instead, when a foreign device is implanted for percutaneous access, epidermal cells begin to migrate, each seeking to surround itself completely with other similar cells. The epidermal cells thus grow down the sides of the device in an attempt to expel it. Deep sinus tracts form and body fluids are exuded at the interface between the device and adjacent tissue, forming a bed for infection. The percutaneous device, if not expelled spontaneously, must be removed to allow the infection to be cured.

Another drawback of presently available skin penetration devices relates to the difficulty of correcting problems with tubes mounted to, and extending through, such devices. Catheter tubes which are used, for example, in continuous ambulatory peritoneal dialysis or continuous infusion of drugs may become misaligned, kinked, blocked or coated with fibrin. With existing technology such catheters cannot readily be removed without disturbing the percutaneous access device, and thus they must be surgically removed and replaced with another access device at a different site. Current technology does not, therefore, readily permit multiple use of an implanted percutaneous access device wherein one catheter may be substituted for another, nor does it allow catheter removal followed by plugging of the device for use at a later time.

Furthermore, advances in surgical techniques coupled with increased emphasis on outpatient surgery have fueled the need for safe, reliable, non-traumatic access for non-invasive intra-body diagnostic and therapeutic follow-up procedures in ambulatory patients.

One such advance is the new surgical technique known as video-laparoscopy. A tubular instrument of small diameter, having a video lens and sampling, biopsy and dissecting instruments, as well as laser output at its tip, is inserted through a small opening through the skin and muscle tissue of a patient. A skilled surgeon directs the tip of instrument to the site of problematic tissue. The laser output is then employed to cut through or destroy problematic tissue.

While this technique represents a major advance over traditional surgical procedures for treatment of a variety of intraabdominal diseases, including cancer, repeated invasive access under general anesthesia is required in many of these instances.

SUMMARY OF THE INVENTION

This invention relates to a surgical access device which is implantable beneath the skin of a patient (i.e. a subcutaneous surgical access device). The device includes a plate made of a resilient biocompatible material. In a preferred embodiment, the resilient material is a metal (e.g., stainless steel or titanium). Attachment points are provided in the plate for securing the plate subcutaneously. For example, the attachment points can be suture holes.

The device also includes an access formed by a slit through the plate having opposed edges. A flexible skirt is attached to the plate at the opposed edges of the slit. The skirt protrudes inwardly toward the bodily cavity from the surface of the plate.

In a preferred embodiment, an air inlet, for the introduction of air into the bodily cavity, is incorporated into the resilient plate. The air inlet can be, for example, a biocompatible valve.

This invention facilitates repeated non-traumatic access for therapeutic or diagnostic purposes. Only local anesthesia is required and most procedures, which today require that the patient be admitted for up to a week or more in the hospital, can be carried out on an outpatient basis as laparoscopy and video-surgery becomes widely available.

The device is particularly useful for abdominal access. Videolaparoscopic treatment in the abdominal cavity can be used to treat, for example, subacute appendicitis, bowel tumors and adhesions, gallstones, liver lesions and gynecological problems (e.g., fibroid tumors, endometriosis, ectopic pregnancies, etc.).

BRIEF DESCRIPTION OF THE DRAWINGS

FIG. 3 is a cross-sectional view of the device taken along lines III—III of FIG. 1 and further including sectional details of the device as implanted in the body of a patient.

FIG. 4 is a top view of a video-laparoscopy access adaptor.

FIG. 5 is a cross-sectional view of an optional embodiment of the invention.

DETAILED DESCRIPTION OF THE INVENTION

Figure 1:
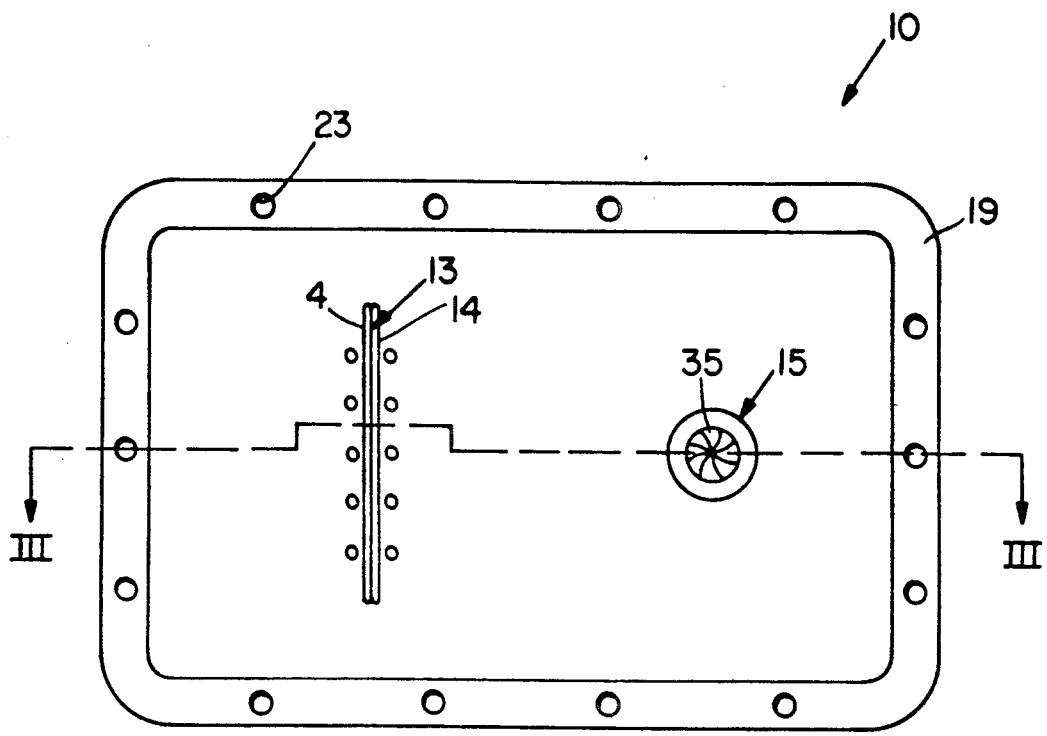
FIG. 1 is a top view of the device with the access closed.

The surgical access device of this invention comprises a resilient biocompatible generally planar plate 10, as shown in FIG. 1. Resilient, as used herein, refers to the tendency of the plate to resume its original form after being bent, compressed or stretched. Resilient, biocompatible materials include, for example, stainless steel or titanium.

The plate 10 includes attachment points for securing the plate subcutaneously (i.e., under the skin). Attachment points can include, for example, suture grommets 12 with holes 23 through which stitching is used to secure the plate subcutaneously to muscular tissue 25, as shown in FIG. 3. In a preferred embodiment, as shown in FIG. 1, suture gromets holes 12 are made around the periphery or border 19 of the plate, and around the periphery of the slit 13 which is described below.

The plate is preferably of rectangular shape extending longitudinally 7 to 10 centimeters and 4 to 6 centimeters in width. The plate is secured in a frame or border 19, which is thicker than the plate. The border 19 provides a clamping surface for holding slit 13 open, as will be explained below.

Figure 2:
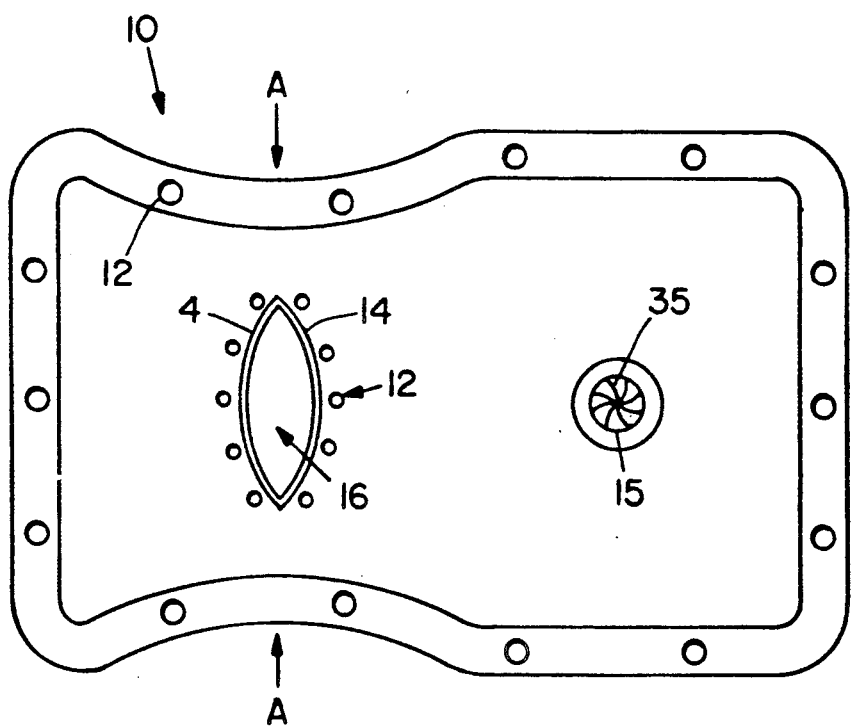
FIG. 2 is a top view of the device with the access open.

An access is formed in the plate by forming a slit 13 (FIG. 1) through the planar surface of the plate, the slit having first and second opposed edges 14, 4 from which a skirt 17 extends transverse the plane of the plate (See FIG. 3). In a preferred embodiment, the slit is oriented transverse to the longitudinal axis of the plate. When the plate is subjected to an appropriate force (i.e., opposing forces pointing inward transverse the longitudinal axis of the plate, as shown by arrows A—A in FIG. 2), the opposed edges 4 and 14 of the slit part to form an access opening 16. The size of the access opening 16, and therefore the length of the slit 13 and the size of the plate, is determined by the diameter of the instrument (e.g., video-laparoscope) to be inserted. In order to help maintain the pneumoperitoneum and minimize air leaks, the lids (or lips) 4 and 14 of the slit 13 are coated with a rubberized silicone to form a smooth lip and provide a reasonably snug fit for the laparoscope tool to be inserted through the slit.

As shown in FIG. 3, the skirt 17, which is preferably an extension of the rubberized silicone, is secured to the plate at the opposed edges of the slit. The skirt protrudes inwardly toward the body cavity approximately 1 to 3 centimeters, depending on the thickness of the skin tissue 26 and depth and thickness of the peritoneum wall 29.

Preferably, as shown in FIG. 1, the surgical access device contains an air inlet 15 for the introduction of air into the bodily cavity. The air inlet also contains a one-way valve 35 which will permit air to pass into the body (e.g. from a compressed air source) but will not permit air to pass from the body outward. Many types of valves suitable for this purpose are known in the art.

In use, the surgical access device is implanted beneath the skin 26 of the patient, as shown in FIG. 3. In an operating room, under sterile conditions, an incision is made through the skin 26 and the muscle tissue or muscle wall 25.

The plate 10 is then secured in the body of the patient by suturinq the periphery of the plate 19 to the muscle wall 25. The periphery of the slit 13 is also sutured to the peritoneum wall 29 and an incision made in the peritoneum wall 29 to permit skirt 17 to extend into the abdominal cavity 30.

When implanted in position, the skirt protrudes through the peritoneum, as shown in FIG. 3, thereby preventing closure and adhesion at the lips of the incision. Thus, when an appropriate force is applied (e.g., opposing forces transverse the longitudinal axis of the plate and coincident with the slit axis, as indicated by the arrows A—A in FIG. 2), the access opens thereby spreading the lips of the incision and providing access opening 16 to the abdominal cavity 30 through the skirt 17. The opposing forces A—A can be applied with an appropriate tool (e.g., a surgical clamp), not shown.

With the access open, the tip of the video-laparoscope, or other appropriate instrument, is inserted into the body. A sealing material (not shown) surrounds the instrument at the access thereby forming an airtight seal. Alternatively, or in addition, an adapter plate 50, as shown in FIG. 4, with an opening 52 to accept the laparoscope tool(s), may be provided. Plate 50 is oval shaped to form an airtight seal with the laparoscope tool(s) and the access opening 16 and may be secured to the plate 10 after the slit is opened by suitable fasteners, such as hooks or Velcron or adhesives, etc. The plate 50 should be made of biocompatible resilient polymer material, which can readily yield to the movement of the laparoscope tool(s) and is formed in a honeycombed, or corregated construction. Air is introduced into the cavity 30 through one-way valve 35 incorporated in the plate by making a small puncture in wall 29.

Following the procedure, the valve 35 is opened to relieve pressure in the body cavity. Force along A—A is applied to more fully access the opening 16, and the surgical instrument is removed. The force is then released and the access opening 16 closes due to the resilient nature of the device. The skin 26 is pulled back and re-sutured in position to cover the device.

Repeated non-traumatic access is gained by cutting the skin 26 along the slit opening 13 to expose the device and applying an appropriate force to open the access and by applying air to access the peritoneum. Following the procedure, the skin is repositioned to cover the device and sutured closed. The skin heals with time, completely covering the implant, but without the problems associated with percutaneous implants.

An optional embodiment of the invention is shown in FIG. 5, wherein the valve 15 is also sutured to the peritoneum wall 29. In this embodiment, tabs 47 are formed on the periphery of the valve 15 with suture holes (not shown) to enable the valve to be sutured in place upon implantation over an opening formed in wall 29.

Current techniques require multiple blind de-novo abdominal wall incisions and/or punctures to create pneumoperitoneum and allow insertion of laparoscopic instruments. The blind insertion of such rigid instruments may cause organ damage, rupture of adhesions, or bleeding. With the subcutaneous device of this invention in place, a passageway free of adhesions is provided. The device of this invention represents a solution to the problems associated with the blind puncture approach and will enable more widespread use of laparoscopy.

Equivalents

Those skilled in the art will recognize or be able to ascertain, using no more than routine experimentation, many equivalents of the specific embodiments of the invention described herein. Such equivalents are intended to be encompassed by the following claims. For example, the slit may be a straight line as shown, or curvilinear.

I claim:

1. A surgical access device for sub-cutaneous implantation in a patient in a space adjacent a bodily cavity for providing convenient access to an incision made in said cavity, comprising:
    a) a resilient plate extending in a first plane;
    b) attachment points for securing the plate subcutaneously;
    c) an access in the plate formed by a deformable slit extending through the plate and
    d) a skirt extending from the slit in a direction transverse the first plane a sufficient distance, such that when the plate is implanted, the skirt extends between the incision sub-cutaneously for preventing closure of the incision.

2. A surgical access device according to claim 1, wherein the plate contains an air inlet for the introduction of air into the bodily cavity.

3. A surgical access device of claim 1, wherein the plate is composed of a biocompatible metal.

4. A surgical access device of claim 2, wherein the attachment points are suture holes.

5. A surgical access device of claim 3, wherein the suture holes are positioned around the periphery of the device, around the periphery of the slit, and around the periphery of the air inlet.

6. A surgical access device of claim 1, wherein the plate is reinforced by a border of material thicker than the plate.

7. A surgical access device of claim 1, wherein the plate is rectangular and the slit extends transverse the longitudinal axis.

8. A surgical access device of claim 1, wherein the slit has smooth opposed lips.

9. A surgical access device for sub-cutaneous implantation in a patient in a space adjacent the abdominal cavity for providing convenient access to an abdominal incision, comprising:
   a) a planar bio-compatible plate extending in a plane;
   b) an access in the plate formed by a slit through the plate, the slit having first and second opposed edges;
   c) suture holes in the plate for securing the plate subcutaneously, the suture holes located around the periphery of the plate and around the periphery of the slit; and
   d) a skirt protruding from the surface of the plate at the access in a direction transverse the plane of the plate for insertion between the incision sub-cutaneously to prevent complete closure of said incision and prevent buildup of tissue adhesions.

10. A method for repeated surgical access to an incision made in a bodily cavity of a patient, comprising:
   a) implanting a surgical access device adjacent the bodily cavity in the patient, the device comprising a resilient plate extending in a first plane with an access slit through the plate and a skirt extending from the slit in a plane transverse the plane of the plate and extending between the incision subcutaneously to prevent closure of the incision;
   b) subjecting the plate to a force which opens the access slit and opening the skirt to access the cavity;
   c) removing the force to close the access slit; and
   d) repeating steps b) and c) as necessary for repeated access to the cavity.

11. The method of claim 10, wherein the slit is oriented transverse to the longitudinal axis of the plate and the plate is subjected to opposing forces in a direction coincident with the axis of the slit.

12. The method of claim 10, wherein the plate is implanted by suturing the periphery of the plate to muscle tissue and suturing the periphery of the access slit around the incision formed in the bodily cavity.

13. A method for repeated non-traumatic surgical access to a bodily cavity of a patient, comprising:
   a) implanting a surgical access device beneath the skin in the muscle wall adjacent the bodily cavity wall in the patient, the device comprising:
      i) a resilient plate;
      ii) attachment points for securing the plate subcutaneously;
      iii) an access formed by an opening in the surface of the plate; and
      iv) a skirt protruding from the surface of the plate toward the bodily cavity; the skirt being inserted into the body subcutaneously through an incision made in the wall of the cavity; and the implanting comprising securing the periphery of the plate to the muscle wall and the periphery of the access to the cavity wall; and
   b) opening the access to perform a surgical procedure.

14. A method for repeated non-traumatic surgical access to the abdominal cavity of a patient through an incision, comprising:
   a) implanting a surgical access device in a space adjacent the incision in the abdominal cavity of a patient between the skin tissue and the peritoneum, the device comprising a plate with a reinforced border and an access lit, the slit being oriented in a direction transverse to the longitudinal axis of the plate with a skirt protruding from the surface of the plate and extending between the incision subcutaneously into the abdominal cavity, said implanting including the steps of:
      (i) securing the border to muscle wall tissue;
      (ii) inserting the skirt through the incision formed in the peritoneum to prevent closure and adhesion of said incision; and
      (iii) securing the periphery of the slit to the periphery of the opening in the peritoneum.

15. The method of claim 14 including the steps of:
   b) subjecting the plate to force which opens the access slit;
   c) removing the force to close the access slit; and
   d) repeating steps b) and c) as necessary for repeated access to the cavity.

16. The method of claim 14 including the step of providing inward flow of fluid in the peritoneum through a valve formed in the plate.

17. The method of claim 16 including covering the access slit with an oval shaped adapter plate when the slit is opened, said adapter plate having an opening to permit a tool to be inserted therethrough without substantial loss of fluid.

18. The device of claim 9 including a valve formed in the plate for applying air into the cavity.

19. The device of claim 18 including an oval adapter plate for covering the slit when opened, While allowing tool access to the cavity without substantial loss of air.

* * * * *

UNITED STATES PATENT AND TRADEMARK OFFICE
CERTIFICATE OF CORRECTION

PATENT NO. : 5,082,005
DATED : Jan. 21, 1992
INVENTOR(S) : Antoine Kaldany

It is certified that error appears in the above-identified patent and that said Letters Patent is hereby corrected as shown below:

Col. 6, line 23, delete "lit" and insert ---slit---.

Signed and Sealed this

First Day of June, 1993

Attest:

MICHAEL K. KIRK

Attesting Officer

Acting Commissioner of Patents and Trademarks